United States Patent [19]

Lex

[11] Patent Number: 4,492,840
[45] Date of Patent: Jan. 8, 1985

[54] APPARATUS FOR INDUCTIVELY HEATING METALLIC MEDICAL AND DENTAL TOOLS

[76] Inventor: August Lex, Entermühlstr. 3, 8221 Grabenstätt, Fed. Rep. of Germany

[21] Appl. No.: 392,150

[22] Filed: Jun. 25, 1982

[30] Foreign Application Priority Data

Mar. 1, 1980 [DE] Fed. Rep. of Germany ....... 3007982

[51] Int. Cl.³ .................. H05B 6/14; A61C 19/00
[52] U.S. Cl. ................... 219/10.57; 219/10.49 R; 219/10.79; 219/10.77; 219/518; 219/227; 219/242; 219/502; 433/28; 433/32; 433/61; 340/687; 250/215; 250/578
[58] Field of Search ............... 219/10.57, 10.41, 10.43, 219/10.79, 10.49 R, 10.67, 10.75, 10.77, 221, 227, 240, 241, 242, 502, 518; 433/28, 32, 49, 53, 61; 340/686, 687; 422/21, 22; 250/206, 215, 578, 209

[56] References Cited

U.S. PATENT DOCUMENTS

| | | | |
|---|---|---|---|
| 1,789,475 | 1/1931 | Powell | 219/242 X |
| 2,620,433 | 12/1952 | Denneen et al. | 219/10.57 |
| 3,422,273 | 1/1969 | Biernson | 250/578 X |
| 3,436,171 | 4/1969 | Weichselbaum et al. | 219/242 X |
| 3,783,276 | 1/1974 | Allington | 250/578 |
| 4,278,870 | 7/1981 | Carleton et al. | 219/518 X |
| 4,308,011 | 12/1981 | Liefke | 250/215 X |

FOREIGN PATENT DOCUMENTS

| | | | |
|---|---|---|---|
| 0052666 | 6/1982 | European Pat. Off. | 433/32 |
| 2911565 | 9/1980 | Fed. Rep. of Germany | 219/10.57 |

Primary Examiner—P. H. Leung
Attorney, Agent, or Firm—Orrin M. Haugen; Thomas J. Nikolai; Douglas L. Tschida

[57] ABSTRACT

An induction heating process and apparatus for flameless heating of metallic dental laboratory tools, medical instruments, and the like. The induction heating coil is energized by placement of instruments within the annular zone formed by the windings of the coil, and differential light sensors are utilized to compensate for variations in ambient light levels.

6 Claims, 2 Drawing Figures

APPARATUS FOR INDUCTIVELY HEATING METALLIC MEDICAL AND DENTAL TOOLS

BACKGROUND OF THE INVENTION

The invention concerns an apparatus for heating metallic dental laboratory tools, instruments and medical implements, wherein the heating is accomplished by means of electrical induction.

A very frequently recurring routine task in dental laboratories consists of modeling workpieces consisting of wax or similar low melting point materials, in the form of wax bite impressions and the like through means of special medical and dental instruments and spatula tools, spatula knives, and the like, consisting of metal. Frequently serving to heat these tools are bunsen burners with an open flame which, for reasons of convenience, are maintained continuously in operation, even when a corresponding heating process for a tool is not required over a long period of time. This leads to the fact that, in large rooms that are occupied with a correspondingly large number of workers, each of whom has available a bunsen burner, a highly elevated space temperature prevails that is in turn compensated for by air conditioning or opening of windows and, from the point of view of energy savings, is to be avoided. Moreover, the air in the room is also made worse overall by the continual comsumption of oxygen which is needed for combustion.

SUMMARY OF THE INVENTION

The task for the invention is to obtain a process and an apparatus for heating tools and instruments for dental laboratories, medical laboratories, medical practitioners, etc., more simply, rapidly and safely. The task is resolved in accordance with the invention: relative to the process, corresponding to the feature of heating with electrical induction; relative to the use of an apparatus containing an induction coil embedded in an insulating substance. Advantageous arrangements of the invention are disclosed herein.

Achieved by the idea of the invention is that the apparatus to be used for heating a tool, e.g. an instrument or wax knife in a dental laboratory, in contrast to the bunsen burner, consumes essential energy only when the corresponding tool is being heated, whereby heat transfer occurs with an essentially improved degree of efficiency over that achieved in the case of a bunsen burner, while during the period of nonuse, the energy need is practically, negligibly small.

In this manner in the present invention, in turn, because of lack of open flames, no reduction of oxygen content occurs in the air of the room in question, and the room temperature is not raised in undesired fashion by the lost energy. While in the case of the known apparatus, for strong heating of metal workpieces, the annular shaped coils are arranged in a fixed position, since we are dealing here exclusively with industrial manufacturuing methods. In the case of the object of the present invention, the coil can be angularly offset in random fashion so that a user can easily introduce into the cross section of the coil the tool that is to be heated, without any peculiar dislocations of the arm or wrist.

Apparatus for inductive heating have, indeed, already become known, which, however, are concerned primarily with industrial hardening or annealing of metal workpieces. By appropriate selection of the frequency, generally above 100,000 Hz, it is possible here, adjusting to the depth of penetration of heating with sufficient accuracy so that, in particular, a surface hardening is possible while the core of the workpiece retains the original, favorable values of a high notch impact strength. The temperatures transferred to the metal workpieces in doing this quite generally lie considerably above 600° K., for which reason an apparatus for heating metal bodies to temperatures lying just slightly above normal room temperature has not been applied.

In an advantageous embodiment in accordance with the invention, the induction coil is embedded in an insulating substance. Additionally, it is, for example, via a pivot arm, lockably held at any angle through a stationary base and can, therefore, be brought into as optimal as possible a working position.

In a preferred form of embodiment of the invention, in the stationary base and/or on the outside of the induction coil there is provided a light emitting diode that indicates the switched-on status of a power circuit for excitation of the induction coil. Through this means, it is possible to easily check visually whether an instrument introduced into the induction coil is actually being heated.

In a form of embodiment in accordance with the invention a switching mechanism is provided, preferentially in the form of a light barrier, via which heating of the dental laboratory tool is effected.

In a preferred form of embodiment in accordance with the invention, the alternating frequency of the induction coil is 22 to 300 kHz, preferentially 50 to 150 kHz.

Demonstrating itself to be particularly favorable in accordance with the invention, is that the power for the apparatus lies between 20–600 Watts, hence it is extremely low.

Here it can be established that a dental laboratory tool, for example with a thickness of 1.5 mm and a length of 10 mm, can be heated to over 500° C. within one minute.

Also futher demonstrating itself to be particularly favorable, is that the energy required in no-load operation amounts to less than 50 Watts.

Further advantages, particulars and features of the invention are obtained in the following with the aid of the example of embodiment explained by the drawings.

IN THE DRAWINGS

FIG. 1: an example of embodiment of an apparatus in accordance with the invention in simplified block diagram representations;

FIG. 2: a structural unit, in a side view and a view from the front, respectively, forming a component part of the apparatus in accordance with FIG. 1 and to be installed on a table surface.

DESCRIPTION OF THE PREFERRED EMBODIMENT

Figure 1:
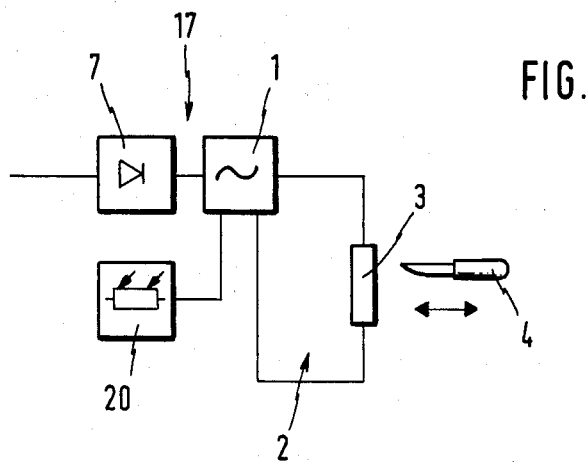

The apparatus illustrated in the drawing includes an alternating current generator 1 and an oscillatory circuit 2 at its output, the reactance of which 3 is structured as a coil having an internal cross section that is adequately sized for introducing a spatula knife 4. The coil windings are embedded in a material such that an annular-shaped induction coil embedded in an insulator is provided which results in an annular induction heater 5 which is adjustable via a pivot arm 6.

As is obtained, in particular from FIG. 1, connected ahead of the inverter 2 is a rectifier 7. Provided further is a switching arrangement 20 that is actuated by photoresistances 18 in the stationary base 8. For example, if an instrument to be heated is introduced into the induction heater 5, light leakage of the natural or artificial light in the room decreases such that, because of this, switching arrangement 20 switches on the power circuit 17 for excitation of the induction coil 5. Capable of being further provided in the switching arrangement 20 are threshold value discriminators, not shown in any further detail.

In the example of embodiment shown, the two photoresistances are driven differentially, i.e. that, upon introduction of an instrument, only the light leakage onto the photoresistance lying in front of the induction heater 5 will be reduced, with the laterally lying photoresistance 18a being drawn upon as the reference measurement value point. In this fashion, capable of being achieved in the case of all light ratios is a trouble-free switch-in and switch-out of the induction heater.

As soon as the power circuit 17 is switched on and the induction heater 5 excited, a light emitting diode 14 lights up at the same time and, therewith, indicates that heating of the instrument introduced is taking place.

Figure 2:
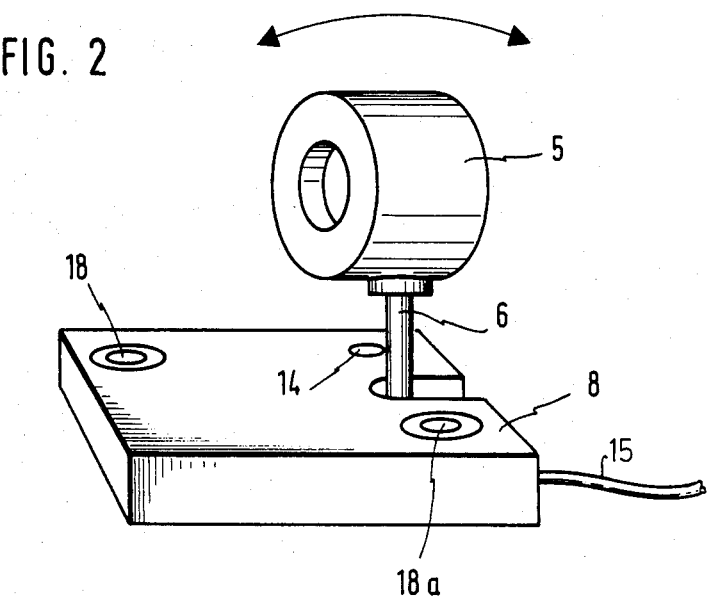

As is obtained from FIG. 2, the annular shaped insulated induction heater 5 is connected, via a piece of cable 15, with a separate structural unit that accommodates the alternating current generator 1 and possible the rectifier 7. Resulting through this separate construction are space advantages, since the apparatus itself can be embodied small and compact. However, it is also possible that the power circuit 17 be arranged in integrated fashion in the stationary base or in the induction heater.

The alternating generator 1 furnishes a frequency between 22 to 300 kHz, preferentially between 50 to 150 kHz, since heating of the tool and/or the spatula knife is desired over its entire cross section and not only superficially. A lower frequency than 22 kHz is unpleasant, since here the audible range is reached.

Total power for the apparatus amounts to 20 to 600 Watts, preferentially 100 to 300 Watts, hence is very low when, for example, this is compared with large induction devices of fields of technology which, for example, require power from 6–8 kW.

Additionally, the no-load running power, provided no dental laboratory tool is to be heated, amounts to less than 50 Watts, for example only 30 or even only 10 Watts, and is, therefore, practically negligible.

If, for example, in accordance with the invention a dental tool with a thickness of 1.5 mm and a height of 10 mm is brought into the induction heater, then this dental laboratory tool will be heated to 500° C. within one minute, wherefrom the advantages in accordance with the invention are clearly visible.

Moreover, regulation of the heating process can also be accomplished via a switching mechanism, preferentially via a light barrier, in such fashion that, upon introduction of a dental laboratory tool or instrument into the induction heater, the heating process is controlled by interruption of the light barrier. Other embodiments of a switching mechanism, for example by pressure impacting, etc., are just as possible.

I claim:
1. In an apparatus for heating metallic medical and dental laboratory tools, instruments and implements by means of exposure to a high frequency electrical field and including an electrically conductive induction coil embedded in an insulator with an annular cavity formed therewithin, said apparatus further comprising:
   (a) said induction coil being pivotally secured to a stationary base by means of a pivot arm linkage;
   (b) a light emitting diode for indicating the operational status of a circuit providing power to said induction coil is visibly mounted on the outer surface of said stationary base;
   (c) said induction coil being arranged for mechanical and electrical coupling to a source of alternating current power; and
   (d) a photosensitive switching circuit and mechanism being provided for controlling the energization of said alternating current power source, said photosensitive switching circuit and mechanism including two photoresistive elements with the first of said photoresistive elements being installed within said stationary base such that it continues to be exposed to light when work is introduced into the confines of said induction coil, and with the second of said photoresistive elements being installed within said stationary base and adjacent said annular cavity such that it is at least partially obstructed from light when work is introduced and present in the confines of said induction coil.

2. An apparatus as defined in claim 1 being particularly characterized in that said induction coil is driven at a frequency of between about 22 and 300 kHz.

3. An apparatus as defined in claim 2 wherein said driving frequency is between 50 and 150 kHz.

4. An apparatus as defined in claim 1 being particularly characterized in that said induction coil is powered at between 20 and 600 watts.

5. An apparatus as defined in claim 4 wherein said induction coil is powered from 100 to 300 watts of power.

6. An apparatus as defined in claimed 1 characterized in that said induction coil has a no-load power consumption of about 50 watts.

* * * * *